(12) United States Patent
Romero

(10) Patent No.: US 9,186,495 B2
(45) Date of Patent: Nov. 17, 2015

(54) METHODS FOR MAKING ENHANCED END PORTIONS OF LEADS OF ELECTRICAL STIMULATION SYSTEMS

(71) Applicant: BOSTON SCIENTIFIC NEUROMODULATION CORPORATION, Valencia, CA (US)

(72) Inventor: Daniel James Romero, Newhall, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 240 days.

(21) Appl. No.: 14/080,380

(22) Filed: Nov. 14, 2013

(65) Prior Publication Data

US 2014/0150957 A1    Jun. 5, 2014

Related U.S. Application Data

(60) Provisional application No. 61/732,802, filed on Dec. 3, 2012.

(51) Int. Cl.
| | | |
|---|---|---|
| *A61N 1/05* | (2006.01) | |
| *H01R 43/20* | (2006.01) | |
| *H01R 4/18* | (2006.01) | |
| *H01R 24/58* | (2011.01) | |

(52) U.S. Cl.
CPC ........ *A61N 1/05* (2013.01); *H01R 43/20* (2013.01); *A61N 1/0551* (2013.01); *H01R 4/18* (2013.01); *H01R 24/58* (2013.01); *H01R 2201/12* (2013.01)

(58) Field of Classification Search
CPC ......... A61N 1/05; A61N 1/0551; H01R 4/18; H01R 24/58

USPC .................................................. 607/115–117
See application file for complete search history.

(56) References Cited

U.S. PATENT DOCUMENTS

| | | | |
|---|---|---|---|
| 4,628,943 A * | 12/1986 | Miller | A61N 1/056 607/127 |
| 4,909,263 A * | 3/1990 | Norris | A61N 1/0524 600/551 |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 6,895,276 B2 * | 5/2005 | Kast | A61N 1/3752 607/37 |
| 7,244,150 B1 | 7/2007 | Brase et al. | |
| 7,437,193 B2 | 10/2008 | Parramon et al. | |
| 7,672,734 B2 | 3/2010 | Anderson et al. | |

(Continued)

*Primary Examiner* — Jeff Aftergut
(74) *Attorney, Agent, or Firm* — Lowe GrahamJones PLLC; Bruce E. Black

(57) ABSTRACT

A method of forming a lead includes providing an elongated lead body defining an annular groove disposed around a circumference of the lead body along one of a distal end or a proximal end of the lead body. A pre-contact is disposed around the circumference of the lead body within the annular groove. The pre-contact includes a pre-contact body having opposing first and second ends and first and second tabs extending outwardly from the opposing first and second ends, respectively. The first and second tabs are crimped together and folded flat against an outer surface of the pre-contact body. A polymeric material of the lead body is re-flowed to facilitate coupling of the pre-contact to the lead body. An outer surface of the pre-contact body is ground down to form a contact disposed along the one of the distal end or the proximal end of the lead body.

20 Claims, 11 Drawing Sheets

(56) References Cited

U.S. PATENT DOCUMENTS

| | | |
|---|---|---|
| 7,761,165 B1 | 7/2010 | He et al. |
| 7,949,395 B2 | 5/2011 | Kuzma |
| 8,224,450 B2 | 7/2012 | Brase |
| 2003/0073348 A1* | 4/2003 | Ries .................... A61N 1/3752 439/578 |
| 2005/0165465 A1 | 7/2005 | Pianca et al. |
| 2006/0173520 A1* | 8/2006 | Olson .................. A61M 25/02 607/115 |
| 2007/0150036 A1 | 6/2007 | Anderson |
| 2007/0219595 A1 | 9/2007 | He |
| 2007/0239243 A1 | 10/2007 | Moffitt et al. |
| 2008/0071320 A1 | 3/2008 | Brase |
| 2009/0248095 A1* | 10/2009 | Schleicher ........... A61N 1/0558 607/116 |
| 2011/0172606 A1* | 7/2011 | Olson ..................... A61N 1/05 607/116 |
| 2012/0271393 A1* | 10/2012 | Schleicher ........... A61N 1/0558 607/117 |
| 2013/0013043 A1* | 1/2013 | Barker ................. A61N 1/3752 607/116 |
| 2014/0155967 A1* | 6/2014 | Howard .................. A61N 1/05 607/116 |

* cited by examiner

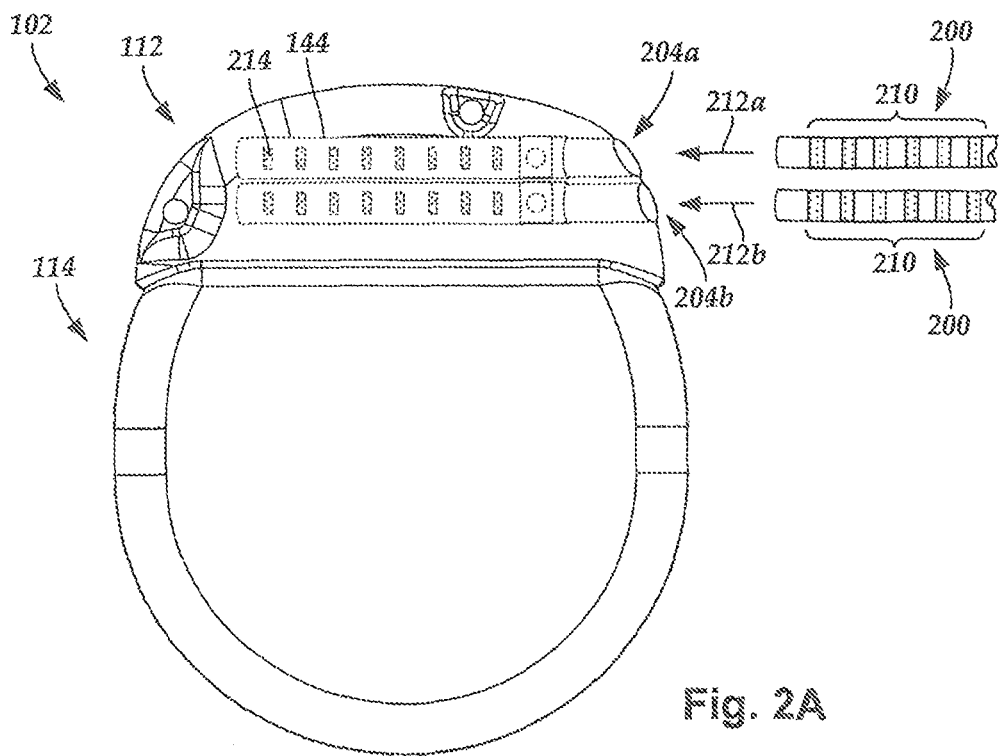

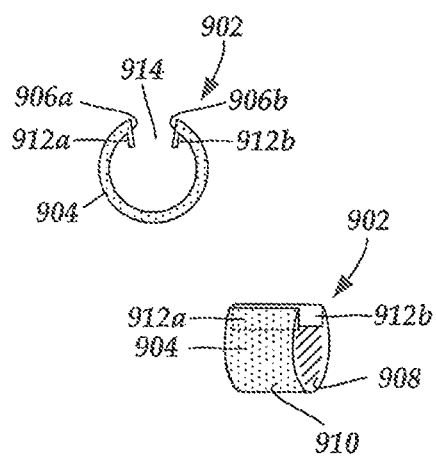
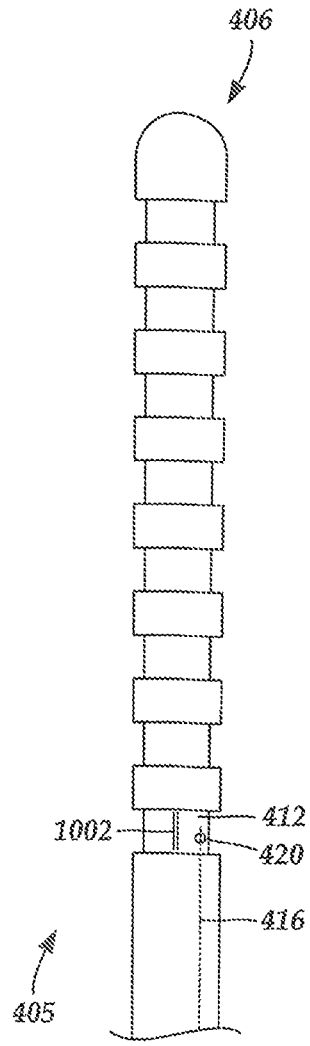
Fig. 9
Fig. 10

METHODS FOR MAKING ENHANCED END PORTIONS OF LEADS OF ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/732,802 filed Dec. 3, 2012, which is incorporated herein by reference.

FIELD

The present invention is directed to the area of implantable electrical stimulation systems and methods of making and using the systems. The present invention is also directed to implantable electrical stimulation leads having end portions configured to receive open-loop contacts that are closable upon being disposed on the leads, as well as methods of making and using the leads, contacts, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a method of forming a lead includes providing an elongated lead body defining at least one annular groove disposed around a circumference of the lead body along one of a distal end or a proximal end of the lead body. For each of the at least one annular groove, a pre-contact is disposed around the circumference of the lead body within the annular groove. The pre-contact includes a pre-contact body having opposing first and second ends and first and second tabs extending outwardly from the opposing first and second ends, respectively. The first and second tabs are crimped together and folded flat against an outer surface of the pre-contact body. A polymeric material of the lead body is re-flowed to facilitate coupling of the pre-contact to the lead body. An outer surface of the pre-contact body is ground down to form a contact disposed along the one of the distal end or the proximal end of the lead body.

In another embodiment, a method of forming a lead includes providing an elongated lead body with at least one annular groove disposed around a circumference of the lead body along one of a distal end or a proximal end of the lead body. At least one slit is formed within each of the at least one annular groove. For each of the at least one annular groove, a pre-contact is disposed around the circumference of the lead body within the annular groove. The pre-contact includes a pre-contact body having opposing first and second ends and first and second tabs extending inwardly from the opposing first and second ends, respectively. The first and second tabs are inserted into the at least one slit. A polymeric material of the lead body is re-flowed to facilitate coupling of the pre-contact to the lead body. An outer surface of the pre-contact body is ground down to form a contact disposed along the one of the distal end or the proximal end of the lead body.

In yet another embodiment, a method of forming a lead includes providing an elongated lead body with at least one annular groove disposed around a circumference of the lead body along one of a distal end or a proximal end of the lead body. For each of the at least one annular groove, a rigid pre-contact is disposed around the circumference of the lead body within the annular groove. The pre-contact includes a pre-contact body having opposing first and second ends. Opposing ends of the pre-contact are squeezed together until opposing ends of the pre-contact come together and wrap around the entire circumference of the lead body. A polymeric material of the lead body is re-flowed to facilitate coupling of the pre-contact to the lead body. An outer surface of the pre-contact body is ground down to form a contact disposed along the one of the distal end or the proximal end of the lead body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2A is a schematic view of one embodiment of the control module of FIG. 1 configured and arranged to electrically couple to an elongated device, according to the invention;

FIG. 9 includes a schematic end view and a schematic side perspective view of yet another embodiment of an open-loop pre-contact suitable for disposing on the lead body end portion of FIG. 4A, the pre-contact including inwardly-directed tabs disposed at opposing ends of the pre-contact, according to the invention;

FIG. 10 is a schematic side view of one embodiment of the lead body end portion of FIG. 4A, the lead body including slots defined in an annular groove, the annular groove configured and arranged to receive the pre-contact of FIG. 9, and the slots defined in the annular groove configured and arranged to receive inwardly-directed tabs disposed on the pre-contact when the pre-contact is disposed in the annular groove, according to the invention;

DETAILED DESCRIPTION

The present invention is directed to the area of implantable electrical stimulation systems and methods of making and using the systems. The present invention is also directed to implantable electrical stimulation leads having end portions configured to receive open-loop contacts that are closable upon being disposed on the leads, as well as methods of making and using the leads, contacts, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; and 7,761,165; and U.S. Patent Applications Publication Nos. 2005/0165465, 2007/0150036; 2007/0219595; 2007/0239243; and 2008/0071320, all of which are incorporated by reference.

Figure 1:
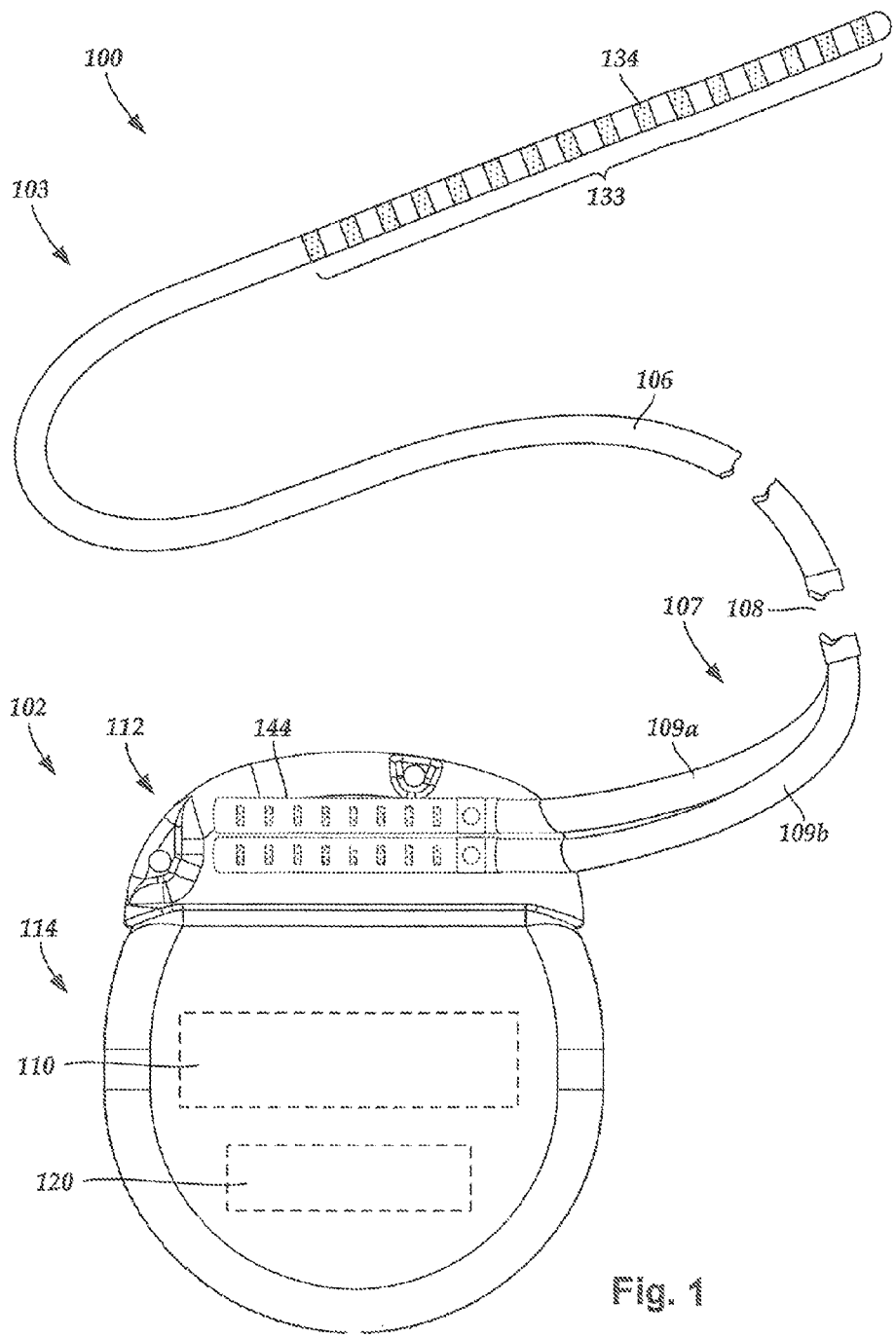
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2B:
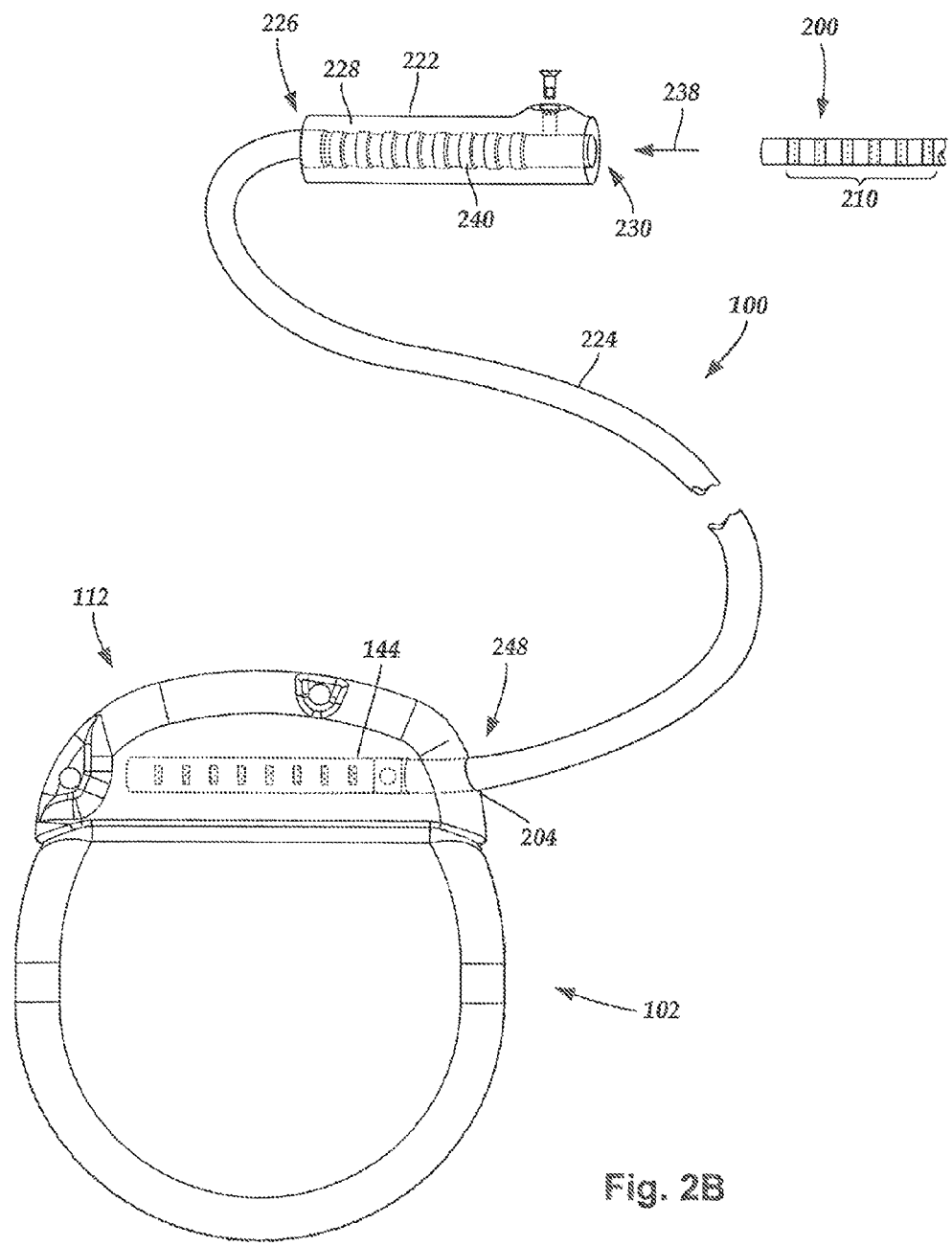
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Conductor wires (not shown) extend from the terminals to the electrodes 134. Typically, one or more electrodes 134 are electrically coupled to each terminal. In at least some embodiments, each terminal is only connected to one electrode 134.

The conductor wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the lead body 106, for example, for inserting a stylet to facilitate placement of the lead body 106 within a body of a patient. Additionally, there may also be one or more lumens (not shown) that open at, or near, the distal end of the lead body 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Figure 3:
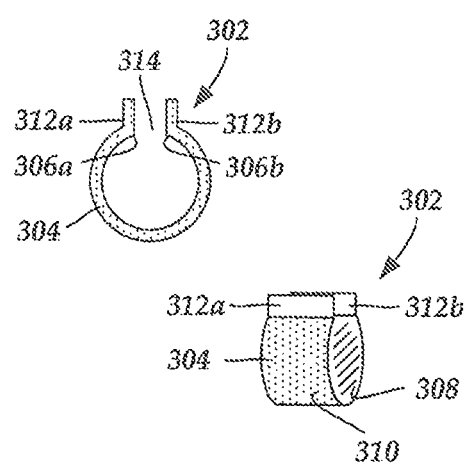
FIG. 3 includes a schematic end view and a schematic side perspective view of one embodiment of an open-loop pre-contact, the pre-contact including outwardly-directed tabs disposed at opposing ends of the pre-contact, according to the invention.

Turning to FIG. 3, at least some conventional leads form contact assemblies by sliding contacts (e.g., terminals and electrodes) onto end portions of the lead body with electrically-nonconductive spacers disposed between adjacent contacts. The contacts and spacers are typically coupled to one another by re-flowing, one or more adhesives, or the like. Forming such contact assemblies may be labor-intensive and provide inconsistent pitches between adjacent contacts. Additionally, forming leads using such techniques may involve blind welding lead conductors to the contacts. Blind welding conductors to contacts may also be labor-intensive and, additionally, may provide inconsistent electrical connections.

As herein described, a technique for disposing contacts (e.g., electrodes or terminals) along end portions of a lead body are described. In at least some embodiments, the contacts are open-loop (i.e., the contacts do not form a continuous loop of material around an open circumference) when disposed on the lead body, and are subsequently crimped or pressed to transition the contacts into closed-loop contacts prior to operation. In at least some embodiments, the contacts are disposed along the end portions of the lead body within annular grooves. In at least some embodiments, the contacts are disposed along the end portions of the lead body without over-molding. In at least some embodiments, the contacts are disposed along the end portions of the lead body without application of one or more adhesives to couple the contacts to the lead body.

Figure 5:
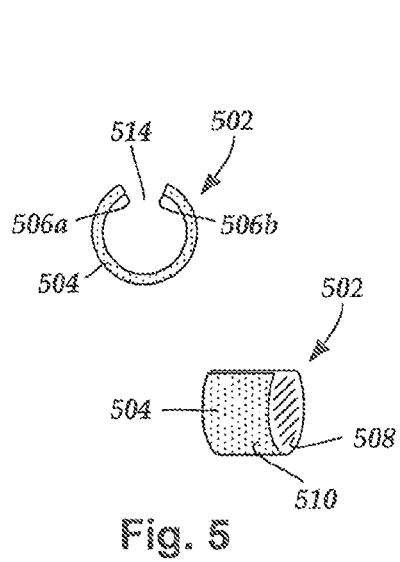
FIG. 5 includes a schematic end view and a schematic side perspective view of a second embodiment of an open-loop pre-contact suitable for disposing on the lead body end portion of FIG. 4A, according to the invention.

FIGS. 3, 5, and 9 describe three different embodiments of open-loop contacts suitable for disposing along end portions of a lead body. Each of the different techniques described herein for disposing the contacts along end portions of lead bodies are described with the contacts being disposed along the distal end portions of the lead body. It will be understood that the contacts, as well as the end portions of the lead body, disclosed herein can be formed, for example, along either (or both) a distal end portion or a proximal end portion of a deep brain stimulation lead, or a percutaneous spinal cord stimulation lead, or the like. Additionally, the contacts, as well as the end portions of the lead body, disclosed herein can be formed, for example, along a proximal end portion of a paddle lead.

In at least some embodiments a pre-contact is open-looped and includes outwardly-directed tabs at opposing ends of the pre-contact. FIG. 3 includes a schematic end view and a schematic side perspective view of one embodiment of an open-loop pre-contact 302. The pre-contact 302 has a body 304 with a first end 306a, an opposing second end 306b, an inner face 308, and an opposing outer face 310. In at least some embodiments, the inner face 308 of the pre-contact 302 includes one or more surface features configured and arranged to facilitate gripping of a surface upon which the inner face 308 abuts.

A first tab 312a is coupled to the first end 306a and a second tab 312b is coupled to the second end 306b. The tabs 312a and 312b are directed outwardly from the body 304 of the pre-contact 302. The pre-contact body 304 may be configured in a variety of shapes. In at least some embodiments, the pre-contact body 304 is annular in shape such that a gap 314 is formed between the first and second ends 306a and 306b, respectively, of the pre-contact 302. The pre-contact body 304 may be configured to have a cross-sectional dimension greater than that of the lead body 106. For example, the pre-contact body 304 may have an outer diameter that is larger than an outer diameter of the lead body 106.

The tabs 312a and 312b may be configured with at least one portion substantially attached to the pre-contact ends 306a and 306b, respectively, while the tabs 312a and 312b extend away from the pre-contact ends 306a and 306b. In at least some embodiments, the tabs 312a and 312b are pivotally attached to the pre-contact ends 306a and 306b, respectively, using one or more swivels or hinges. According to a second example, the tabs 312a and 312b may be joined by a flexible strip of material enabling the tabs 312a and 312b to pivot about the portion attached to the pre-contact ends 306. According to a third example, the tabs 312a and 312b may be integrated as extensions of the pre-contact body 304 such that the tabs 312a and 312b are substantially flexible to pivot about the pre-contact ends 306a and 306b, respectively. Further, the tabs 312a and 312b may be configured with dimensions to substantially cover the gap 314 when folded radially over the pre-contact body 304, discussed later in greater detail.

It will be understand that the degree of flexibility of the tabs 312a and 312b may differ from that of the pre-contact body 304. According to an example, the tabs 312a and 312b may be made relatively more flexible than the pre-contact body 304, such as by using different types or amounts of materials. It will be understood that the tabs 312a and 312b are formed from electrically-conductive material.

Figure 4A:
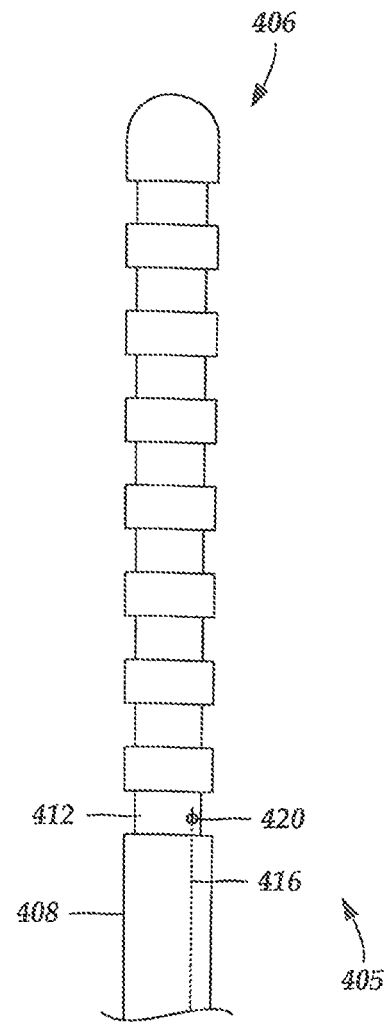
FIG. 4A is a schematic side view of one embodiment of an end portion of a lead body with a plurality of longitudinally-spaced-apart annular grooves each suitable for receiving a different pre-contact of FIG. 3, according to the invention.

FIGS. 4A-4G illustrate one embodiment for disposing the pre-contact 302 at a distal end portion of a lead body. FIG. 4A is a schematic side view of one embodiment of the distal end portion 405 of the lead body 406. According to one example, the distal end portion 405 of the lead body 406 may be annular having a substantially circular cross-section; however, other suitable cross-sectional shapes, for example, elliptical, oval, polygon, irregular, etc. may be employed. The distal end portion 405 of the lead body 406 defines a plurality of annular grooves, such as annular groove 412, along an outer surface 408 of the lead body 406. The annular grooves 412 are configured for receiving the pre-contact 302.

In at least some embodiments, portions of the outer surface 408 of the lead body 406 disposed between adjacent annular grooves 412 form spacers between adjacent contacts, when contacts are disposed in the annular grooves. The spacers are sufficiently long to prevent, or at least reduce, undesired interactions between adjacent contacts when contacts are disposed in the annular grooves 412. It may be advantageous to have a consistent spacing between adjacent annular grooves 412 in order to provide consistent stimulation and consistent target stimulation locations.

In at least some embodiments, one or more apertures, such as aperture 420, are defined in each of the annular grooves 412. The one or more apertures 420 are configured and arranged to receive conductors, such as the conductor 416, extending within the lead body 406. The conductor 416 extends through the aperture 420 and electrically couples the pre-contact 302 to contacts (e.g., terminals) disposed along an opposing end portion of the lead body 406 when the pre-contact 302 is disposed in the annular groove 412.

Figure 4B:
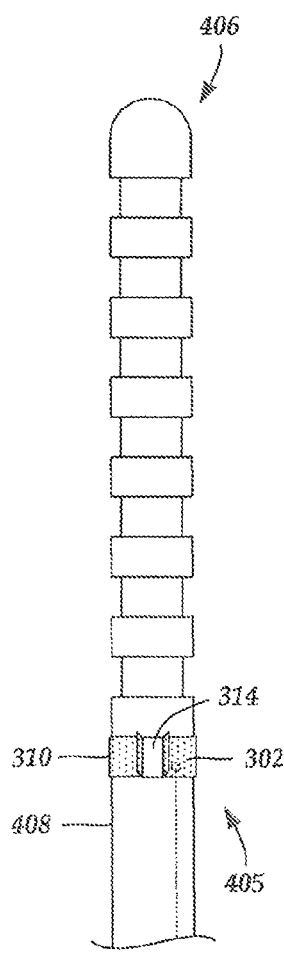
FIG. 4B is a schematic side view of one embodiment of the pre-contact of FIG. 3 disposed over an annular groove formed along the lead body end portion of FIG. 4A, according to the invention.
Figure 4C:
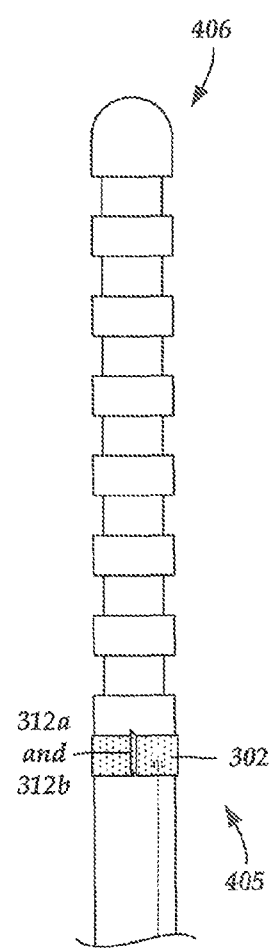
FIG. 4C is a schematic side view of one embodiment of the pre-contact of FIG. 3 disposed over an annular groove defined in the lead body end portion of FIG. 4A with opposing ends of the pre-contact abutting one another and tabs disposed on the opposing ends of the pre-contact crimped together, according to the invention.

FIGS. 4B-4C illustrate one embodiments of disposing the pre-contact 302 along the distal end portion 405 of the lead body 406. As discussed in more detail below, once the pre-contacts are disposed along the lead body, the pre-contacts may be ground down to form contacts.

FIG. 4B is a schematic side view of one embodiment of the pre-contact 302 disposed around most of the circumference of the lead body 406 in the annular groove 412. Lead bodies, such as the lead body 406, are typically not compressible enough to pass through a center portion of a pre-contact, such as the annular pre-contact 302, thereby making it difficult to dispose the pre-contact 302 at its respective location (e.g., within the annular groove 412) during manufacture. Thus, in at least some embodiments the open-loop pre-contact 302 is configured and arranged to be disposed in the annular groove 412 without compressing the lead body 406.

In at least some embodiments, the pre-contact ends 306a and 306b are temporarily moved away from each other, thereby increasing the gap 314 between the pre-contact ends 306a and 306b and also increasing an inner diameter of the pre-contact 302, without causing a permanent deformation in the shape of the pre-contact 302. This increased gap 314 between the opposing pre-contact ends 306a and 306b may enable the pre-contact body 304 to be disposed around the lead body 406 within the annular groove 412. Once disposed within the annular groove 412, the pre-contact 302 may retract to its original annular shape.

Once the pre-contact 302 is disposed in, or in proximity to, the annular groove 412, the pre-contact 302 may be electrically-coupled to the conductor 416. The pre-contact 302 may be electrically-coupled to the conductor 416 in any suitable manner including, for example, laser welding, resistance welding, crimping, electrically-conductive adhesive, soldering, swaging, or the like or combinations thereof.

Turning to FIG. 4C, the gap 314 between the opposing ends 306a and 306b of the disposed open-loop pre-contact 302 does not emit electrical energy for stimulation. Therefore, it may be desirable to close the gap 314 to enable stimulation in all directions around the outer surface of the pre-contact 302. Additionally, closing the gap 314 may facilitate permanently coupling the pre-contact 302 to the lead body 406.

FIG. 4C is a schematic side view of one embodiment of the pre-contact 302 disposed in the annular groove 412. As shown in FIG. 4C, once the pre-contact 302 is disposed within the annular groove 412 and the pre-contact 302 is electrically-coupled to the conductor 416, the tabs 312a and 312b of the pre-contact 302 may be physically brought together to close the gap 314 between the opposing ends 306a and 306b of the pre-contact 302. In at least some embodiments, the tabs 312a and 312b are secured to one another using a variety of methods known in the art such as welding, soldering, using electrically-conductive adhesives, or the like or combinations thereof. In preferred embodiments, the tabs 312a and 312b are crimped together.

Figure 4D:
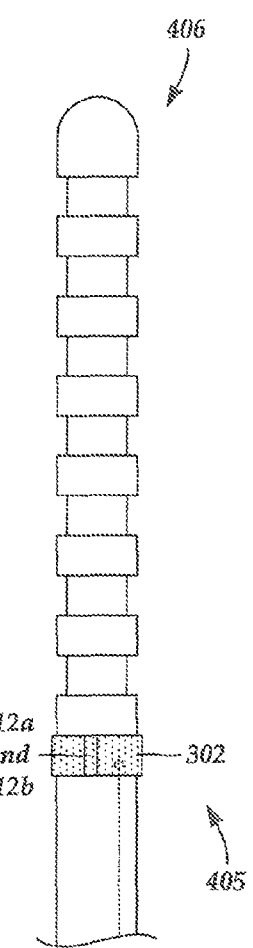
FIG. 4D is a schematic side view of one embodiment of the pre-contact of FIG. 3 disposed over an annular groove defined in the lead body end portion of FIG. 4A with crimped tabs of opposing ends of the pre-contact folded flat against an outer surface of the pre-contact, according to the invention.

As shown in FIG. 4D, once the tabs 312a and 312b of the pre-contact 302 are brought together to close the gap 314 between the opposing ends 306a and 306b of the pre-contact 302, the tabs 312a and 312b may be folded flat against the outer face 310 of the pre-contact 302.

Figure 4E:
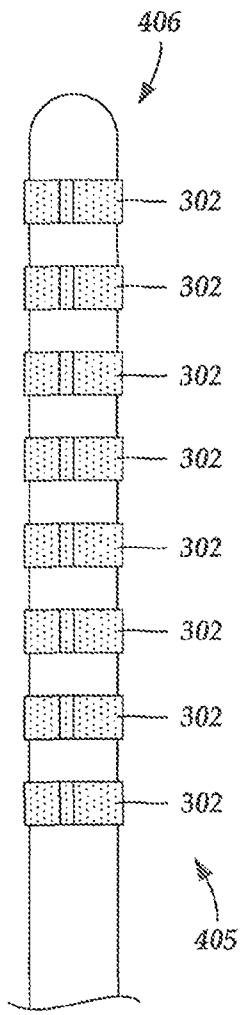
FIG. 4E is a schematic side view of one embodiment of multiple pre-contacts of FIG. 4D disposed over annular grooves formed in the lead body end portion of FIG. 4A, according to the invention.

As shown in FIG. 4E, additional pre-contacts 302 may be similarly coupled to the lead body 406 within other annular grooves 412. Additionally, in at least some embodiments, the tabs 312a and 312b disposed on opposing ends 306a and 306b of the pre-contacts are folded flat over the outer face 310 of the pre-contacts 302.

Figure 4F:
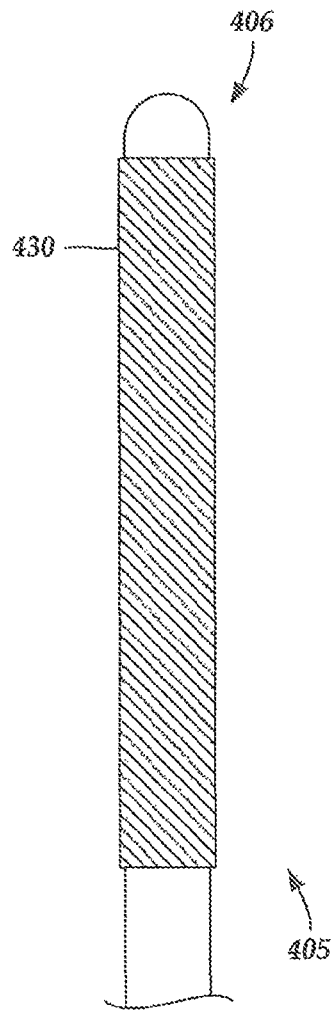
FIG. 4F is a schematic side view of one embodiment of heat shrink tubing disposed over the lead body end portion and the multiple pre-contacts of FIG. 4E, the heat shrink tubing facilitating coupling of the pre-contacts to the lead body end portion during reflowing of material of the lead body end portion, according to the invention.

As shown in FIG. 4F, in at least some embodiments once each of the pre-contacts 302 are disposed in their respective annular grooves 412, the distal end portion 405 of the lead body 406 may be re-flowed to further couple the pre-contacts 302 to the lead body 406. In at least some embodiments, a heat shrink tube 430 is disposed over the end portion (e.g., the distal end portion 405) of the lead body 406. The heat shrink tubing 430 may be used to prevent the pre-contacts 302 from bulging outward during reflowing. The heat shrink tubing 430 may also be used to prevent lead body material from oozing onto outer surfaces 410 of the pre-contacts 302. Subsequent to the reflow process, the heat shrink tube 430 is removed.

Figure 4G:
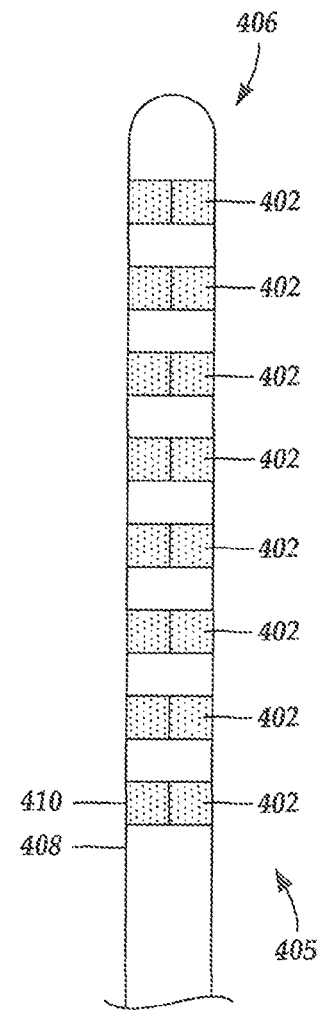
FIG. 4G is a schematic side view of one embodiment of multiple contacts disposed on the lead body end portion of FIG. 4F, the multiple contacts formed by grinding down the multiple pre-contacts of FIG. 4E, according to the invention.

As shown in FIG. 4G, the outer faces 310 of the pre-contacts 302 may be ground down to form contacts 402 with outer faces 410. In at least some embodiments, the outer faces 310 of the pre-contacts 302 are ground down until contacts 402 are formed having outer faces 410 that are isodiametric with the lead body 406. In at least some embodiments, the outer surface 408 of the distal end portion 405 of the lead body 406 is also ground down.

Turning to FIG. 5, in at least some embodiments an open-looped pre-contact does not include tabs. In which case, the open-loop, tab-less pre-contact may be secured to a lead body by application of mechanical force to close an open portion, or gap, between opposing ends of the open-loop, tab-less pre-contact body.

FIG. 5 includes a schematic end view and a schematic side perspective view of another embodiment of a pre-contact 502 with an open-loop suitable for disposing on the lead body 406. The pre-contact includes a body 504 having a first end 506a, an opposing second end 506b, an inner face 508, and an opposing outer face 510. In at least some embodiments, the pre-contact 502 is annular, such that a gap 514 is formed between the ends 506a and 506b. In at least some embodiments, the pre-contact 502 does not include tabs, such as the tabs (312a and 312b of FIG. 3).

The pre-contact body 504 may be configured to have a cross-sectional dimension greater than that of the lead body end portion 406. For example, the pre-contact body 504 may have an outer diameter larger than that of the distal end portion 405 of the lead body 406. One of skill in the art will understand that the pre-contact body 504 may be made sufficiently flexible to allow the opposing pre-contact ends 506a and 506b to move relatively away from each other for expanding an inner diameter of the pre-contact 502.

FIGS. 6-8D illustrate one embodiment of disposing the pre-contact 502 at the distal end portion 405 of the lead body 406. As mentioned above, the techniques described herein can be used to dispose the pre-contact 502 at either end portion (or both end portions) of the lead body 406, and that, for clarity of discussion, the techniques are described for disposing the pre-contact 502 along the distal end portion 405 of the lead body 406.

Figure 6:
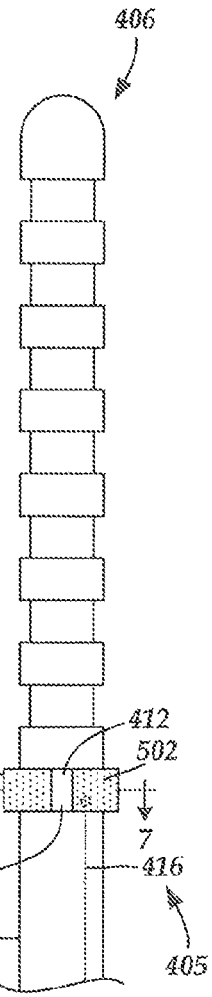
FIG. 6 is a schematic side view of one embodiment of the pre-contact of FIG. 5 disposed over an annular groove formed along the lead body end portion of FIG. 4A, according to the invention.

FIG. 6 is a schematic side view of one embodiment of the pre-contact 502 disposed in one of the annular grooves 412 formed along the distal end portion 405 of the lead body 406. The pre-contact ends 506a and 506b may be moved temporarily away from each other to increase the gap 514 between them for receiving the annular groove 412, while avoiding permanently changing the annular shape of the pre-contact 504. In at least some embodiments, the gap 514 of the pre-contacts 502 has a length that is no smaller than a diameter of the lead body 406 within the annular groove 412. Once the pre-contact 502 is disposed in, or in proximity to, the annular groove 412, the pre-contact 502 is electrically-coupled to the conductor 416.

Figure 7:
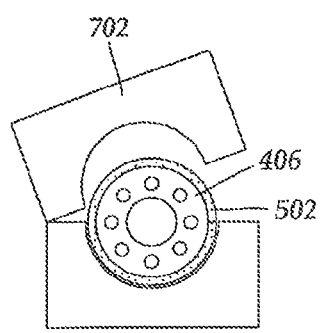
FIG. 7 is a schematic transverse cross-sectional view of one embodiment of the pre-contact of FIG. 5 disposed on the lead body end portion of FIG. 4A, where the pre-contact and lead body end portion are disposed in a tool suitable for squeezing together opposing ends of pre-contact to couple the pre-contact to the lead body end portion, according to the invention.
Figure 8A:
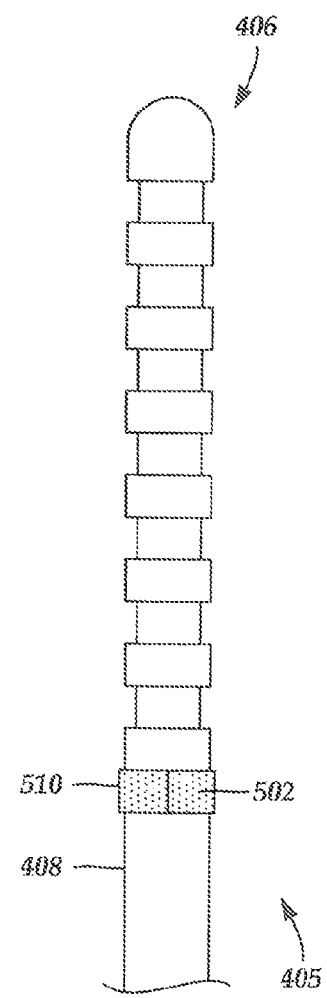
FIG. 8A is a schematic side view of one embodiment of the pre-contact of FIG. 5 disposed over an annular groove formed along the lead body end portion of FIG. 4A, where opposing ends of the pre-contact have been squeezed together using the tool of FIG. 7, according to the invention.

Turning to FIG. 7, once the pre-contact 502 is disposed in the annular groove and electrically-coupled to the conductor 416, mechanical force may be used to squeeze together the pre-contact ends 506a and 506b, thereby coupling the pre-contact 502 to the lead body 406 within the annular groove 412 (see e.g., FIG. 8A).

FIG. 7 is a schematic transverse cross-sectional view of one embodiment of the pre-contact 502 positioned over a portion of the lead body 406. The pre-contact 502 is positioned within a pre-contact squeezing tool 702 configured to apply mechanical force on the pre-contact body 504 to squeeze together the pre-contact ends 506a and 506b, thereby coupling the pre-contact 502 to the lead body 406.

The pre-contact squeezing tool 702 can be formed from any squeezing tool adapted to squeeze together the pre-contact ends 506a and 506b of the pre-contact 502. In at least some embodiments, the pre-contact squeezing tool 702 includes a receiving block and a squeezing block. The receiving block may include a first tool groove for substantially receiving the pre-contact 504 positioned over a portion of the lead body 406. The squeezing block may include a second tool groove configured to press against the pre-contact 504 placed in the receiving block.

Figure 8B:
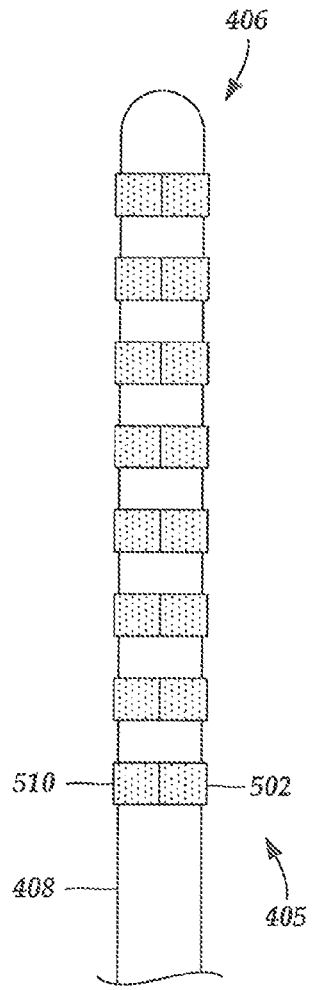
FIG. 8B is a schematic side view of one embodiment of multiple pre-contacts of FIG. 5 disposed over annular grooves formed along the lead body end portion of FIG. 4A, where opposing ends of each of the pre-contacts have been squeezed together, according to the invention.

In at least some embodiments, when the pre-contact squeezing tool 702 is empty and the squeezing block is placed on the receiving block, the dimension of an opening created between the first tool groove and the second tool groove may be configured lesser than a cross-sectional dimension of the pre-contact 504 disposed within the annular groove 412 of the lead body 406. Accordingly, when the squeezing block is operated to apply mechanical force on the pre-contact 502 disposed in the receiving block, the opposing ends 506a and 506b of the pre-contact 502 are squeezed together until the opposing pre-contact ends 506a and 506b come together, thereby coupling the contact 502 to the lead body 406, as shown in FIG. 8A. Similarly, multiple pre-contacts 504 may be coupled to the lead body 406 within the annular grooves 412, as shown in FIG. 8B.

Figure 8C:
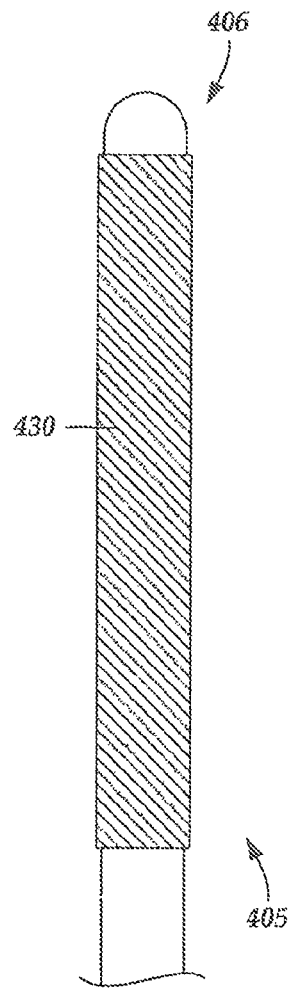
FIG. 8C is a schematic side view of one embodiment of heat shrink tubing disposed over the lead body end portion and the multiple pre-contacts of FIG. 8B, the heat shrink tubing facilitating coupling of the pre-contacts to the lead body end portion during reflowing of material of the lead body end portion, according to the invention.

FIG. 8C illustrates a schematic side view of one embodiment of the heat shrink tube 430 disposed over the distal end portion 405 of the lead body 406 and the pre-contacts 502 disposed thereon. As discussed above with reference to FIG. 4F, in at least some embodiments once each of the pre-contacts 502 are disposed in their respective annular grooves 412, the distal end portion 405 of the lead body 406 may be re-flowed to further couple the pre-contacts 502 to the lead body 406. The heat shrink tubing 430 may be used to prevent the pre-contacts 502 from bulging outward during reflowing. Additionally, the heat shrink tubing 430 may also prevent, or at least reduce, lead body material from oozing onto outer surfaces of the pre-contacts 502. Subsequent to the reflow process, the heat shrink tube 430 is removed.

Figure 8D:
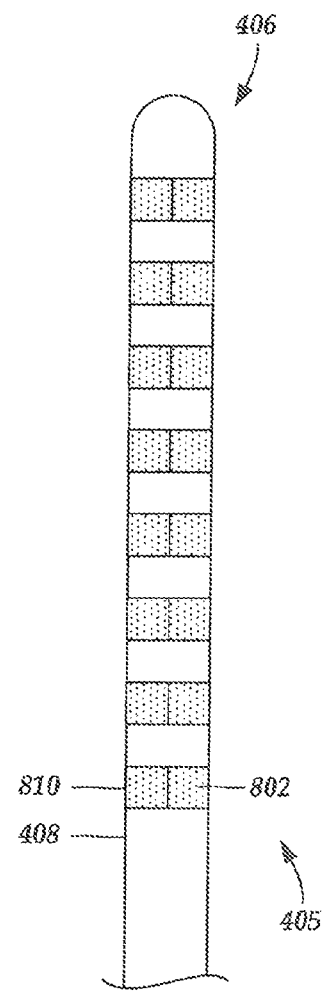
FIG. 8D is a schematic side view of one embodiment of multiple contacts disposed on the lead body end portion of FIG. 8C, the multiple contacts formed by grinding down the multiple pre-contacts of FIG. 8B, according to the invention.

As shown in FIG. 8D, the outer faces 510 of the pre-contacts 408 may be ground down to form contacts 402 with outer faces 810. In at least some embodiments, the outer faces 310 of the pre-contacts 302 are ground down until the contacts 402 are formed having outer faces 810 that are isodiametric with the lead body 406. In at least some embodiments, the outer surface 408 of the distal end portion 405 of the lead body 406 is also ground down.

Turning to FIG. 9, in at least some embodiments an open-loop pre-contact includes inwardly-directed tabs. In which case, the pre-contact may be coupled to a lead body by application of mechanical force to close an open portion, or gap, between opposing ends of the pre-contact. The inwardly-directed tabs may be inserted into one or more slots formed in the annular groove within which the pre-contact is disposed, the one or more slots facilitating coupling of the pre-contact within the annular groove.

FIG. 9 includes a schematic end view and a schematic side perspective view of yet another embodiment of an open-loop pre-contact 902 suitable for disposing on the lead body 406. The pre-contact 902 has a body 904 with a first end 906a, an opposing second end 906b, an inner face 908, and an opposing outer face 910. A first tab 912a is coupled to the first end 906a and a second tab 912b is coupled to the second end 906b. The tabs 912a and 912b are directed inwardly along the body 904 of the pre-contact 902. The pre-contact body 904 may be configured in a variety of shapes. In at least some embodiments, the pre-contact body 904 is annular in shape such that a gap 914 is formed between the first and second ends 906a and 906b, respectively.

FIGS. 10-12B illustrate one embodiment of disposing the pre-contact 902 along the distal end portion 405 of the lead body 406. The techniques described herein can be used to dispose the pre-contact 902 at either end (or both ends) of the lead body 406, and that, for clarity of discussion, the techniques are described for disposing the pre-contact 902 at the distal end of the lead body 406.

FIG. 10 is a schematic side view of one embodiment of the distal end portion 405 of the lead body 406. The distal end portion 405 of the lead body 406 defines annular grooves, such as annular groove 412. One or more slits 1002 are defined within the annular groove 412. The slits 1002 may be configured to receive the inwardly-directed tabs 912 disposed on the pre-contact 902 when the pre-contact 902 is disposed within the annular groove 412. The aperture 420 is also defined in the annular groove 412. The conductor 416 extends through the aperture 420 from within the lead body 406 and is configured and arranged to electrically couple with the pre-contact 902 when the pre-contact 902 is received by the annular groove 412.

Figure 11:
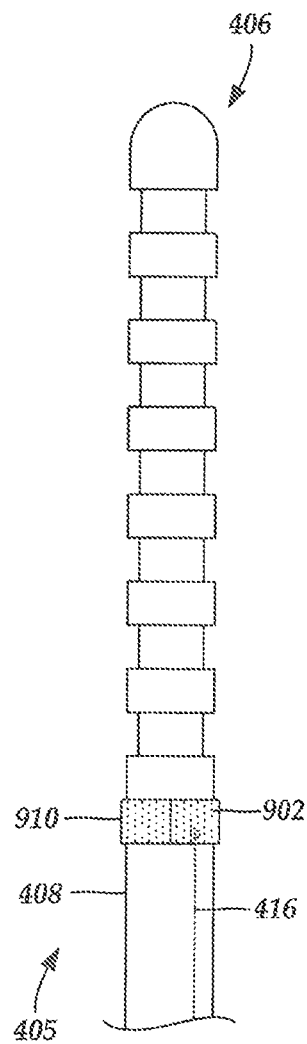
FIG. 11 is a schematic side view of one embodiment of the pre-contact of FIG. 9 disposed over an annular groove formed along the lead body end portion of FIG. 10, according to the invention.

FIG. 11 is a schematic side view of one embodiment of the pre-contact 902 disposed within the annular groove 412. The inwardly-directed tabs 912 are inserted within the one or more slits 1002 and the conductor 416 is coupled to the pre-contact 902. In at least some embodiments, the inwardly-directed first tab 912a is inserted in a first slit of the one or more slits 1002 and the second tab 912b is inserted in a second slit of the one or more slits 1002. In other embodiments, both the first and the second tabs 912a and 912b are inserted in a single slit 1002. In at least some embodiments, the opposing ends 906a and 906b of the pre-contact 902 are squeezed together to couple the pre-contact 902 to the lead body 406 in the annular groove 412. In at least some embodiments, the opposing ends 906a and 906b of the pre-contact 902 are squeezed together using the pre-contact squeezing tool (702 in FIG. 7).

In at least some embodiments, a different pre-contact 902 is disposed along each of the annular grooves 412, with the corresponding tabs 912a and 912b of each of the pre-contacts 902 disposed in one or more slits 1002 defined in each of the annular grooves 412. In at least some embodiments, a different conductor 416 is coupled to each pre-contact 902. In at least some embodiments, the distal end portion 405 of the lead body 406 is re-flowed, as described above. In at least some embodiments, the heat shrink tube 430 is used to facilitate the re-flowing process, as also described above.

Figure 12A:
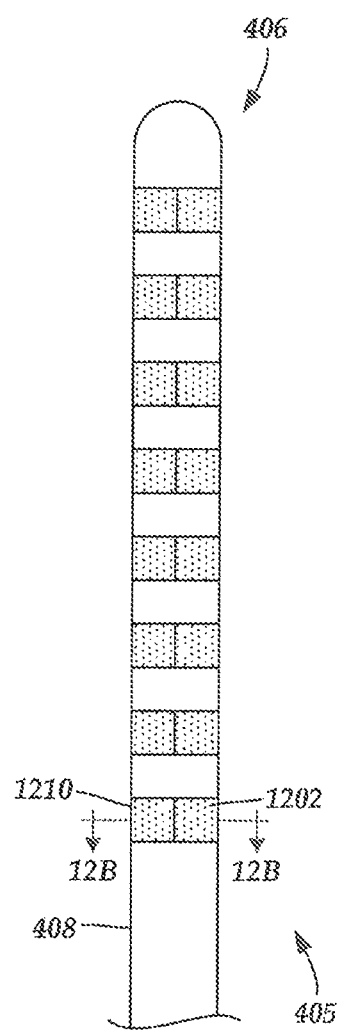
FIG. 12A is a schematic side view of one embodiment of multiple contacts disposed on the lead body end portion of FIG. 4A, the multiple contacts formed by disposing multiple pre-contacts of FIG. 9 in annular grooves defined in the lead body end portion and grinding down the multiple pre-contacts, according to the invention.
Figure 12B:
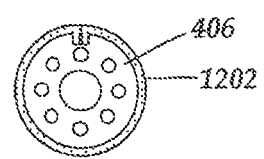
FIG. 12B is a schematic transverse cross-sectional view of one embodiment of a contact disposed on the lead body end portion of FIG. 4A, the contact formed by disposing the pre-contact of FIG. 9 in an annular groove defined in the lead body end portion and grinding down the pre-contact, according to the invention.

FIG. 12A is a schematic side view of one embodiment of contacts 1202 disposed along the distal end portion 405 of the lead body 406. FIG. 12B is a schematic transverse cross-sectional view of one embodiment of one of the contacts 1202 disposed along the distal end portion 405 of the lead body 406. As shown in FIGS. 12A-12B, the outer faces 910 of the pre-contacts 902 may be ground down to form contacts 1202 with outer faces 1210. In at least some embodiments, the outer faces 910 of the pre-contacts 902 are ground down until the formed contacts 1202 have outer faces 1210 that are isodiametric with the lead body 406. In at least some embodiments, the outer surface 408 of the distal end portion 405 of the lead body 406 is also ground down.

Figure 13:
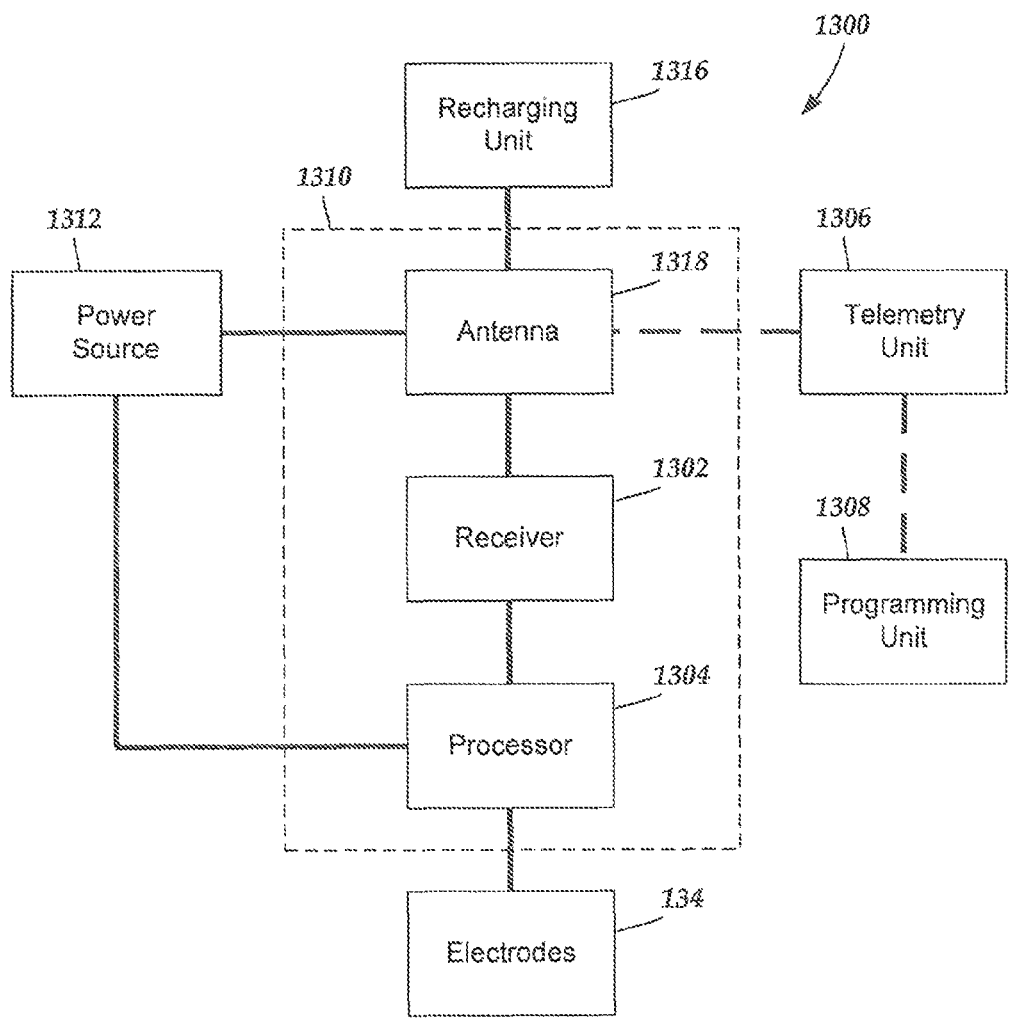
FIG. 13 is a schematic overview of one embodiment of components of a stimulation system, including an electronic subassembly disposed within a control module, according to the invention.

FIG. 13 is a schematic overview of one embodiment of components of an electrical stimulation system 1300 including an electronic subassembly 1310 disposed within a control module. It will be understood that the electrical stimulation system can include more, fewer, or different components and can have a variety of different configurations including those configurations disclosed in the stimulator references cited herein.

Some of the components (for example, power source 1312, antenna 1318, receiver 1302, and processor 1304) of the electrical stimulation system can be positioned on one or more circuit boards or similar carriers within a sealed housing of an implantable pulse generator, if desired. Any power source 1312a and 312b can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1318 or a secondary antenna. The external power source can be in a device that is mounted on the skin of the user or in a unit that is provided near the user on a permanent or periodic basis.

If the power source 1312a and 312b is a rechargeable battery, the battery may be recharged using the optional antenna 1318, if desired. Power can be provided to the battery for recharging by inductively coupling the battery through the antenna to a recharging unit 1316 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1304 is generally included to control the timing and electrical characteristics of the electrical stimulation system. For example, the processor 1304 can, if desired, control one or more of the timing, frequency, strength, duration, and waveform of the pulses. In addition, the processor 1304 can select which electrodes can be used to provide stimulation, if desired. In some embodiments, the processor 1304 may select which electrode(s) are cathodes and which electrode(s) are anodes. In some embodiments, the processor 1304 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1308 that, for example, allows modification of pulse characteristics. In the illustrated embodiment, the processor 1304 is coupled to a receiver 1302 which, in turn, is coupled to the optional antenna 1318. This allows the processor 1304 to receive instructions from an external source to, for example, direct the pulse characteristics and the selection of electrodes, if desired.

In one embodiment, the antenna 1318 is capable of receiving signals (e.g., RF signals) from an external telemetry unit 1306a and 306b which is programmed by a programming unit 1308. The programming unit 1308 can be external to, or part of, the telemetry unit 1306. The telemetry unit 1306a and 306b can be a device that is worn on the skin of the user or can be carried by the user and can have a form similar to a pager, cellular phone, or remote control, if desired. As another alternative, the telemetry unit 1306a and 306b may not be worn or carried by the user but may only be available at a home station or at a clinician's office. The programming unit 1308 can be any unit that can provide information to the telemetry unit 1306a and 306b for transmission to the electrical stimulation system 1300. The programming unit 1308 can be part of the telemetry unit 1306a and 306b or can provide signals or information to the telemetry unit 1306a and 306b via a wireless or wired connection. One example of a suitable programming unit is a computer operated by the user or clinician to send signals to the telemetry unit 1306.

The signals sent to the processor 1304 via the antenna 1318 and receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1300 to cease operation, to start operation, to start charging the battery, or to stop charging the battery. In other embodiments, the stimulation system does not include an antenna 1318 or receiver 1302 and the processor 1304 operates as programmed.

Optionally, the electrical stimulation system 1300 may include a transmitter (not shown) coupled to the processor 1304 and the antenna 1318 for transmitting signals back to the telemetry unit 1306a and 306b or another unit capable of receiving the signals. For example, the electrical stimulation system 1300 may transmit signals indicating whether the electrical stimulation system 1300 is operating properly or not or indicating when the battery needs to be charged or the level of charge remaining in the battery. The processor 1304 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method of forming an electrical stimulation lead, the method comprising:
   providing an elongated lead body defining at least one annular groove disposed around a circumference of the lead body along one of a distal end or a proximal end of the lead body;
   for each of the at least one annular groove, disposing a pre-contact around the circumference of the lead body within the annular groove, the pre-contact comprising a pre-contact body having opposing first and second ends and first and second tabs extending outwardly from the opposing first and second ends, respectively;
crimping together the first and second tabs;
folding the crimped first and second tabs flat against an outer surface of the pre-contact body;
reflowing a polymeric material of the lead body to facilitate coupling of the pre-contact to the lead body; and
grinding an outer surface of the pre-contact body to form a contact disposed along the one of the distal end or the proximal end of the lead body.

2. The method of claim 1, wherein disposing a pre-contact around the circumference of the lead body comprises, for each of the at least one annular groove, disposing the pre-contact within the annular groove with the pre-contact having an outer diameter that is larger than an outer diameter of the lead body.

3. The method of claim 2, wherein grinding an outer surface of the pre-contact body to form a contact comprises grinding the pre-contact until the outer diameter of the pre-contact is equal to the outer diameter of the lead body.

4. The method of claim 1, wherein disposing a pre-contact around the circumference of the lead body comprises, for each of the at least one annular groove, disposing a pre-contact within the annular groove with the pre-contact comprising a pre-contact body having a front face and an opposing rear face.

5. The method of claim 4, wherein disposing a pre-contact within the annular groove with the pre-contact comprising a pre-contact body having a front face and an opposing rear face comprises electrically coupling the rear face to one of a plurality of conductors.

6. The method of claim 4, wherein disposing a pre-contact within the annular groove with the pre-contact comprising a pre-contact body having a front face and an opposing rear face comprises gripping the annular groove with a plurality of surface features formed along the rear face of the pre-contact.

7. The method of claim 1, wherein reflowing a polymeric material of the lead body comprises disposing heat shrink tubing over the pre-contact prior to reflowing the polymeric material of the lead body.

8. The method of claim 1, wherein grinding an outer surface of the pre-contact body comprises grinding the outer surface of the pre-contact body to form an electrode disposed along the distal end of the lead body.

9. The method of claim 1, wherein grinding an outer surface of the pre-contact body comprises grinding the outer surface of the pre-contact body to form a terminal disposed along the proximal end of the lead body.

10. A method of forming an electrical stimulation lead, the method comprising:
providing an elongated lead body with at least one annular groove disposed around a circumference of the lead body along one of a distal end or a proximal end of the lead body;
for each of the at least one annular groove, forming at least one slit within the annular groove;
for each of the at least one annular groove, disposing a pre-contact around the circumference of the lead body within the annular groove, the pre-contact comprising a pre-contact body having opposing first and second ends and first and second tabs extending inwardly from the opposing first and second ends, respectively;
inserting the first and second tabs into the at least one slit;
reflowing a polymeric material of the lead body to facilitate coupling of the pre-contact to the lead body; and
grinding an outer surface of the pre-contact body to form a contact disposed along the one of the distal end or the proximal end of the lead body.

11. The method of claim 10, wherein forming at least one slit within the annular groove comprises, for each of the at least one annular groove, forming a single slit within the annular groove.

12. The method of claim 11, wherein inserting the first and second tabs into the at least one slit comprises inserting each of the first and second tabs into the single slit.

13. The method of claim 10, wherein forming at least one slit within the annular groove comprises, for each of the at least one annular groove, forming a first slit and a second slit within the annular groove.

14. The method of claim 13, wherein inserting the first and second tabs into the at least one slit comprises inserting the first tab into the first slit and inserting the second tab into the second slit.

15. The method of claim 10, wherein reflowing a polymeric material of the lead body comprises disposing heat shrink tubing over the pre-contact prior to reflowing the polymeric material of the lead body.

16. A method of forming an electrical stimulation lead, the method comprising:
providing an elongated lead body with at least one annular groove disposed around a circumference of the lead body along one of a distal end or a proximal end of the lead body;
for each of the at least one annular groove, disposing a rigid pre-contact around the circumference of the lead body within the annular groove, the pre-contact comprising a pre-contact body having opposing first and second ends;
squeezing the pre-contact together until opposing ends of the pre-contact come together and the pre-contact wraps around the entire circumference of the lead body;
reflowing a polymeric material of the lead body to facilitate coupling of the pre-contact to the lead body; and
grinding an outer surface of the pre-contact body to form a contact disposed along the one of the distal end or the proximal end of the lead body.

17. The method of claim 16, wherein squeezing the pre-contact together comprises using a pre-contact squeezing tool to squeeze the pre-contact together until opposing ends of the pre-contact come together and the pre-contact wraps around the entire circumference of the lead body.

18. The method of claim 16, wherein disposing a rigid pre-contact around the circumference of the lead body within the annular groove comprises, for each of the at least one annular groove, disposing the pre-contact within the annular groove with the pre-contact having an outer diameter that is larger than an outer diameter of the lead body.

19. The method of claim 18, wherein grinding an outer surface of the pre-contact body comprises grinding the outer surface of the pre-contact body until the outer diameter of the pre-contact is equal to the outer diameter of the lead body.

20. The method of claim 16, wherein reflowing a polymeric material of the lead body to facilitate coupling of the pre-contact to the lead body comprises disposing heat shrink tubing over the pre-contact prior to reflowing the polymeric material of the lead body.

* * * * *